(12) United States Patent
Treece et al.

(10) Patent No.: US 7,293,448 B2
(45) Date of Patent: Nov. 13, 2007

(54) ABRASION RESISTANCE TESTING APPARATUS

(75) Inventors: Kimberly R. Treece, Kokomo, IN (US); Brock Gray, Ossian, IN (US)

(73) Assignee: International Truck Intellectual Property Company, LLC, Warrenville, IL (US)

( * ) Notice: Subject to any disclaimer, the term of this patent is extended or adjusted under 35 U.S.C. 154(b) by 282 days.

(21) Appl. No.: 11/121,444

(22) Filed: May 4, 2005

(65) Prior Publication Data
US 2006/0248940 A1    Nov. 9, 2006

(51) Int. Cl.
*G01N 3/56*    (2006.01)

(52) U.S. Cl. ................................. 73/7; 451/5

(58) Field of Classification Search ........... 73/7; 702/34; 451/5
See application file for complete search history.

(56) References Cited

U.S. PATENT DOCUMENTS

| | | | |
|---|---|---|---|
| 4,196,611 A | | 4/1980 | Suga |
| 4,895,102 A | * | 1/1990 | Kachel et al. ............... 118/620 |
| 4,930,258 A | * | 6/1990 | Carlson .......................... 451/5 |
| 5,969,226 A | | 10/1999 | Wert et al. |
| 7,241,200 B2 | * | 7/2007 | Kalanovic ....................... 451/5 |

* cited by examiner

*Primary Examiner*—Thomas P. Noland
(74) *Attorney, Agent, or Firm*—Jeffrey P. Calfa; Gerald W. Askew (57) ABSTRACT

An abrasion resistance testing apparatus tests the abrasion resistance of a test sample. The apparatus has an abrading device in fluid communication with a pneumatic system. The abrading device uses a piston to move an abrading tool onto and off of the test sample. A force measuring sensor cell measures the force provided by the piston and can send a signal to an electronic controller. The electronic controller can be used to control the testing conditions, such as by turning on and off a motor, and opening and closing valves in the pneumatic system to control the force on the abrading tool and test sample and other fluid flow.

10 Claims, 8 Drawing Sheets

ABRASION RESISTANCE TESTING APPARATUS

BACKGROUND OF THE INVENTION

1. Field of the Invention

The present invention relates to an abrasion resistance testing apparatus for materials such as plastics, rubber and fabrics.

2. Description of the Prior Art

In a motor vehicle, hose and tubing failure often results in expensive repair costs. If the vehicle is under warranty, the vehicle manufacturer must replace or repair parts damaged by the hose and tubing failure. If the vehicle is not under warranty, the owner pays the expensive repair costs.

To properly test the abrasion resistance of the outer cover of a hose specimen, the testing method must conform to or exceed ISO 6945 requirements. This standard method of testing compares the quality levels of hose or tubing, but does not predict product abrasion life. The standard method is designed for wire or reinforced hose with smooth and parallel covers.

One of the problems of the ISO 6845 and related abrasion resistance testing devices is the lack of an automated shut-off when the material fails. Without an automated shut-off, the material has to be closely monitored by the user to determine when the material fails and shut off the device. If the device is not shut-off upon material failure, the abrading tip will keep moving across the test sample down to the mandrel, possibly destroying the abrading tip.

Another problem is the prior art devices do not measure the actual load or force applied to the test sample. This leaves the user to estimate the load based on the weight of the abrading tip and other weights added to the abrading tip.

The prior art devices are designed to easily test only one particular outer diameter of tubing. If the user want to test different sizes of tubing, there is no way to easily adjust the test sample to fit under the abrading tip. Similarly, if a different type of material needs to be tested, such as upholstery fabric, one would have to use a different machine to test the fabric.

Therefore, it would be advantageous to develop an abrasion resistance testing apparatus that automatically shuts off when the test sample fails. It would also be advantageous to develop an abrasion resistance testing apparatus that could measure the actual force applied to the test sample. It would be further advantageous to develop an abrasion resistance testing apparatus that could be used with test samples having a variety of outer diameters. An abrasion resistance testing apparatus that could be used to test a variety of test samples, from upholstery fabrics to tubing to rubber would be equally advantageous.

SUMMARY OF THE INVENTION

According to the invention, there is provided an abrasion resistance testing apparatus for testing a test piece using an abrading device in fluid communication with a pneumatic system. The abrading device has an abrading tool, a pneumatic cylinder and a support platform. The pneumatic cylinder has a plate fastened to the abrading tool, and a piston connected to the plate. The piston can move the plate and abrading tool down onto the test piece during testing and retract the plate and abrading tool after testing concludes.

The abrading tool has a force measuring sensor cell connected to the plate. When the piston pushes the plate down and the abrading tool is pushed onto the test piece, the sensor cell measures the force provided by the piston.

Once the abrading tool is on the test piece, the platform slides on rails engaging opposite sides of the platform during the testing. The rails are supported at each end with rail supports attached to a base. A motor attached to the platform moves the platform back and forth and can be used to adjust the frequency of the cycle.

An electronic controller can be programmed to control the testing conditions, such as by turning on and off the motor, and opening and closing valves in the pneumatic system to control the force on the abrading tool. The user uses an interface to establish the testing parameters.

Additional effects, features and advantages will be apparent in the written description that follows.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Turning to the Figures where like reference numerals refer to like structures, an abrasion resistance testing apparatus 10 has an abrading device 12, a support 60 for a test piece 52, an electrical controller 76, a motor 88, a pneumatic system 101 and a base 64.

The abrading device 12 has a platform 14 supporting a pneumatic cylinder 16 and an abrading tool 18. The platform 14 slides with minimal friction along parallel rails 20 during testing. Each end 22, 23 of the rails 20 attaches to a rail support 24, 25 located on top of the base 64.

Sliders 26 attach to opposite sides 28, 29 of the platform 14. Each slider 26 slidingly engages one of the rails 20. The sliders 26 can include bearings or rollers and are preferably oil-free bearing sliders for moving the platform 14 with minimal friction along the rails 20. One example of sliders and rails is an Igus DryLin® T linear guide system.

The abrading tool 18 has an abrading tip 30, a sensor cell 32 and a tip connector 34 connecting the sensor cell 32 to the abrading tip 30. The tip connector 34 can removably attach to the abrading tip 30, the sensor cell 32, or both.

The abrading tip 30 has a rectangular top 128 and a slanted bottom 129 slanting from the top 128 to a curved tip 130. For hose testing, the abrading tip 30 should conform or exceed the ISO 6945:1991(E) specification. The abrading tip 30 therefore has a 45° angle, a height of about 50 mm, a length of about 50 mm and a width of about 25.4 mm. The removable attachment of the tip connector 34 to the abrading tip 30 and/or sensor cell 32 allows the abrading tip 30 to be swapped out of the abrading device 12 for a different size or type of curved tip 130 when testing other materials, such as fabric or corrugated hose. Curved tips 130 can have different angles and be made from different materials, such as other types of steel, nylon or other abrasive materials, when testing items other than hoses.

The sensor cell 32 can be a pancake load cell 36 with a pressure transducer or strain gage 38 and communicates with the electronic controller 76. The strain gage 38 measures the load on the abrading tool 18 and sends an output signal to the electronic controller 76. A signal conditioner can convert the electrical signal from the strain gage 38 from voltage to pressure. The calculated force should range from about 50 N±0.5 N.

The platform 14 has an opening through which at least part of the pneumatic cylinder 16 extends. The pneumatic cylinder 16 is in fluid communication with a supply of pneumatic fluid, such as pressurized air. The pneumatic cylinder 16 has a piston 42 with a plate 40 attached to a piston rod 44. The pneumatic cylinder 16 should have minimal rotation during movement of the abrading device 12, such as a non-rotating pneumatic cylinder with stabilizer rods. One example of pneumatic cylinder 16 is a Parker Hannifin 2MNR Series non-rotating pneumatic cylinder with two stabilizer rods. The pneumatic cylinder 16 has an input cylinder line 46 in fluid communication with a piston input 116 and an output cylinder line 47 in fluid communication with a piston output 117. The plate 40 of the pneumatic cylinder 16 releasably fastens to the abrading tool.

Figure 1:
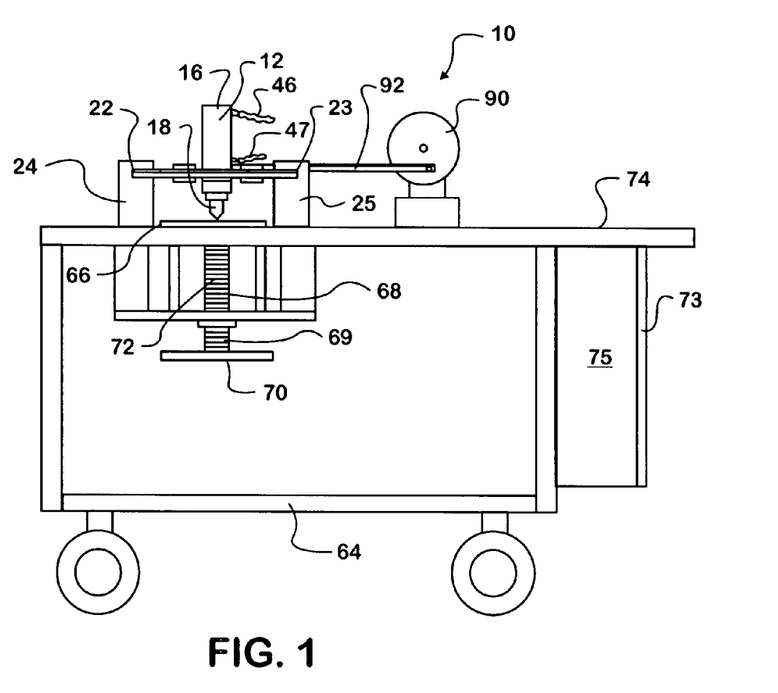
FIG. 1 is a side plan view of an abrasion resistance testing apparatus of the invention with the wiring and pneumatic system removed.
Figure 2:
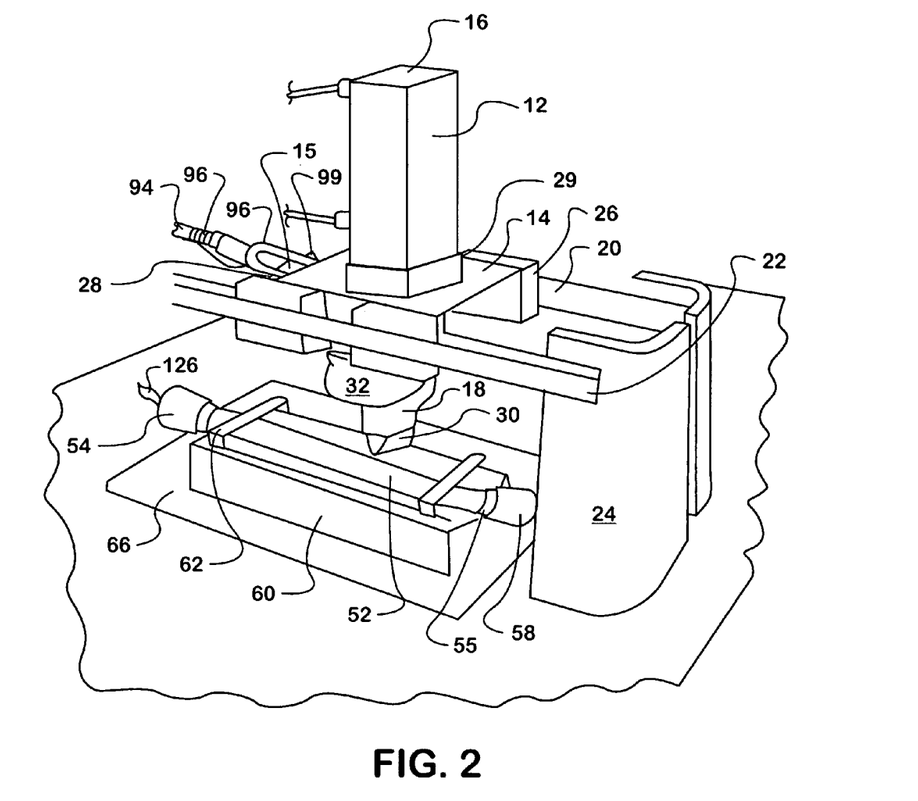
FIG. 2 is a perspective partial view of an abrasion resistance testing apparatus of the invention.
Figure 3:
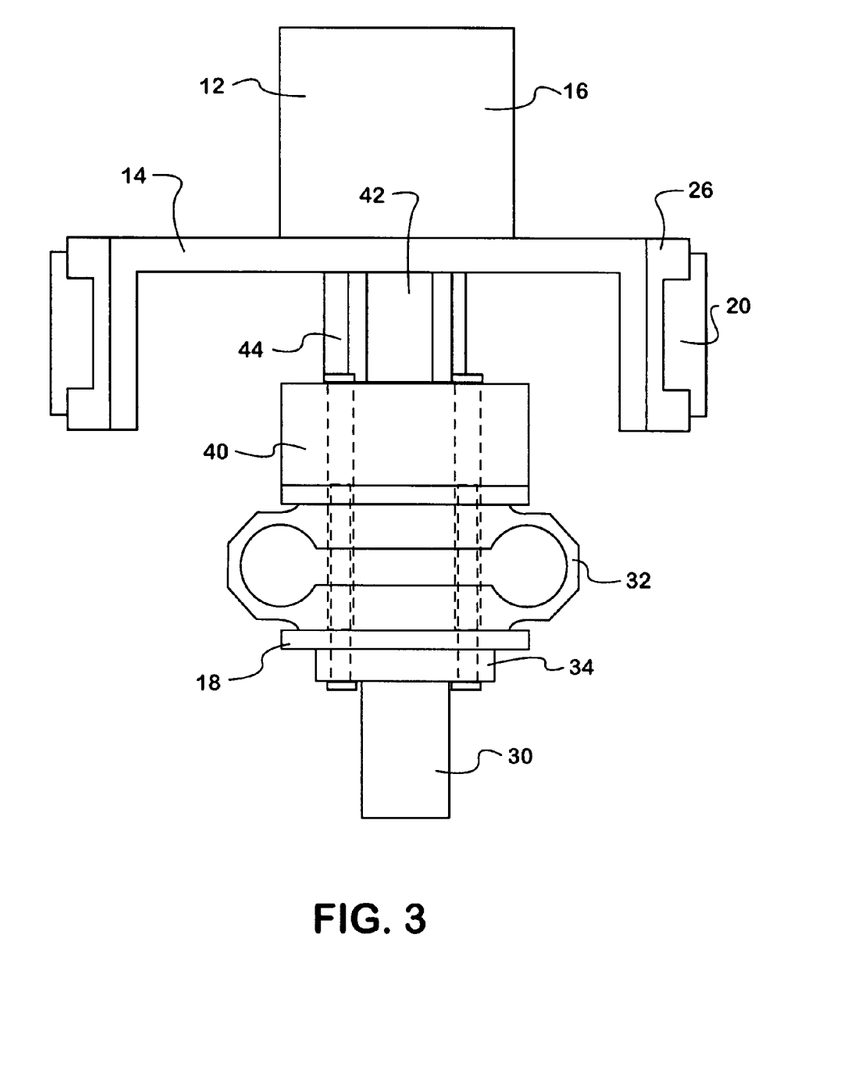
FIG. 3 is a rear partial view of an abrading device of the invention.
Figure 4:
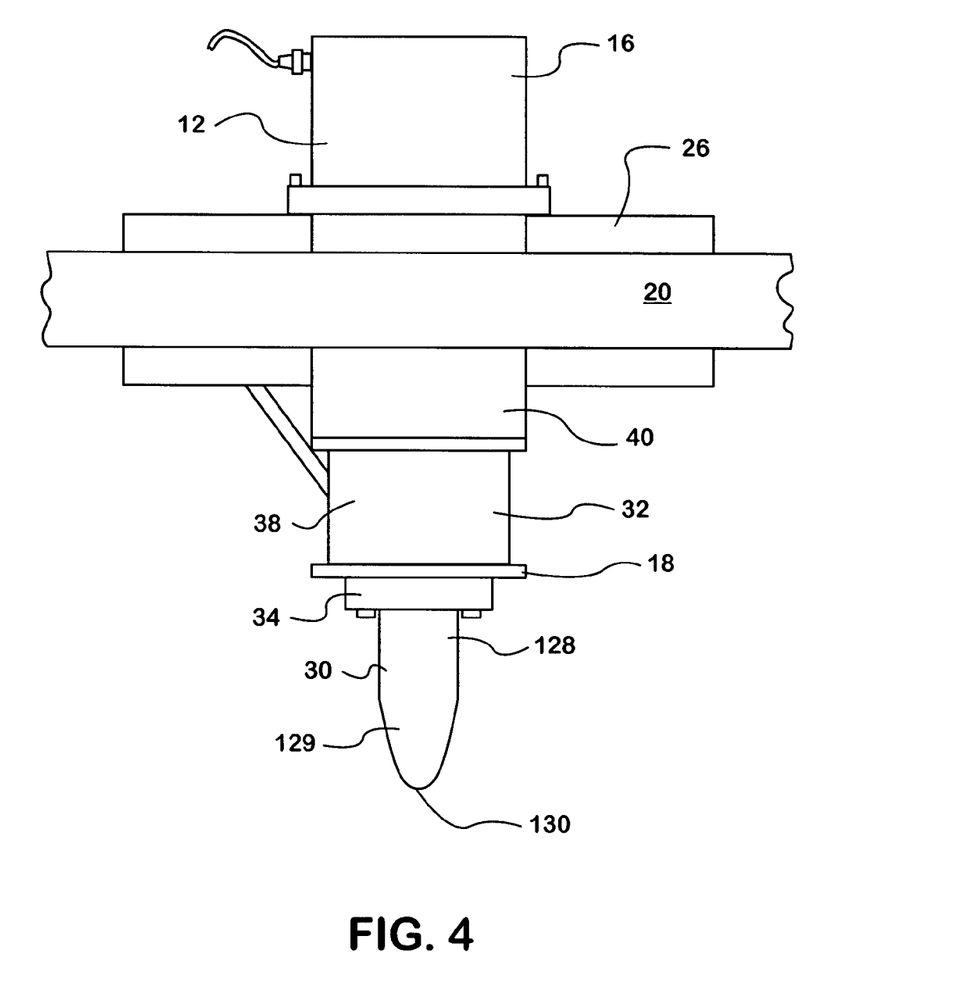
FIG. 4 is a side partial view of an abrading device of the invention.
Figure 5:
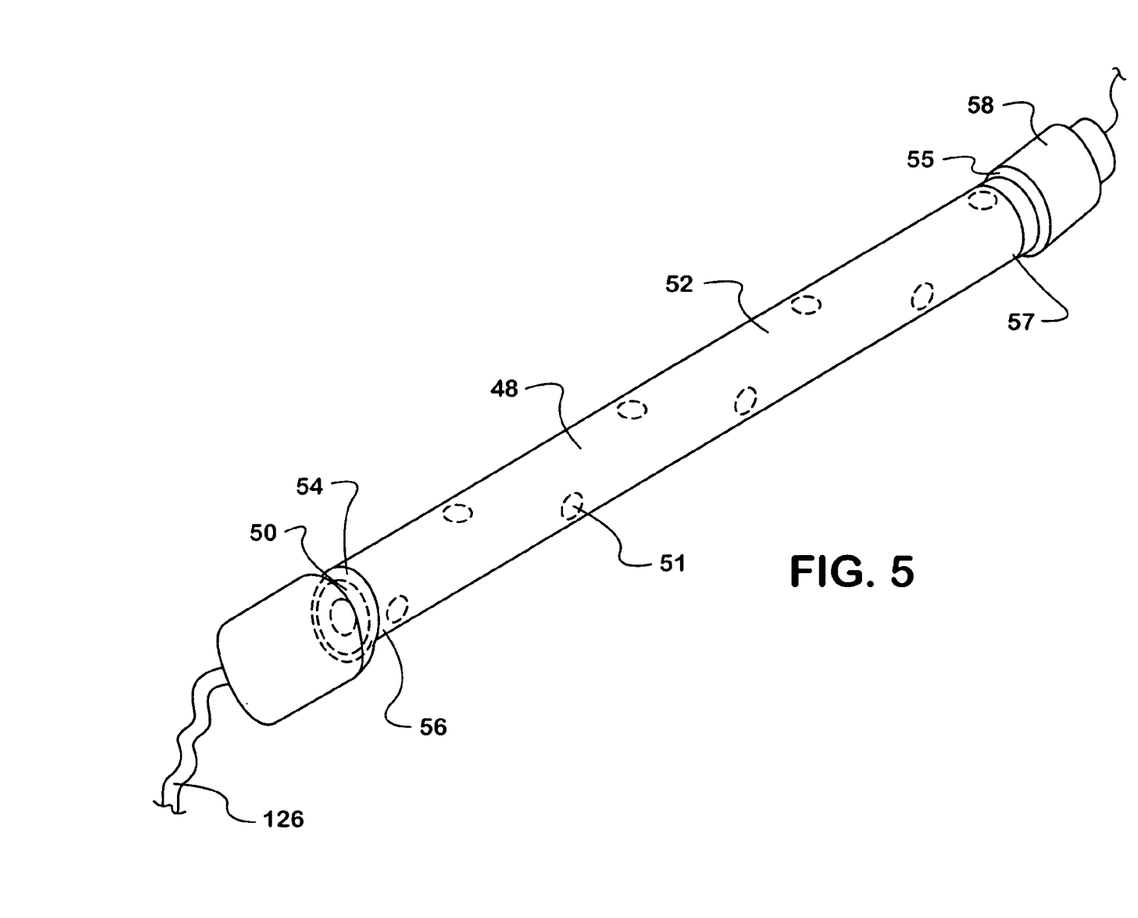
FIG. 5 is a perspective view of a test piece.
Figure 6:
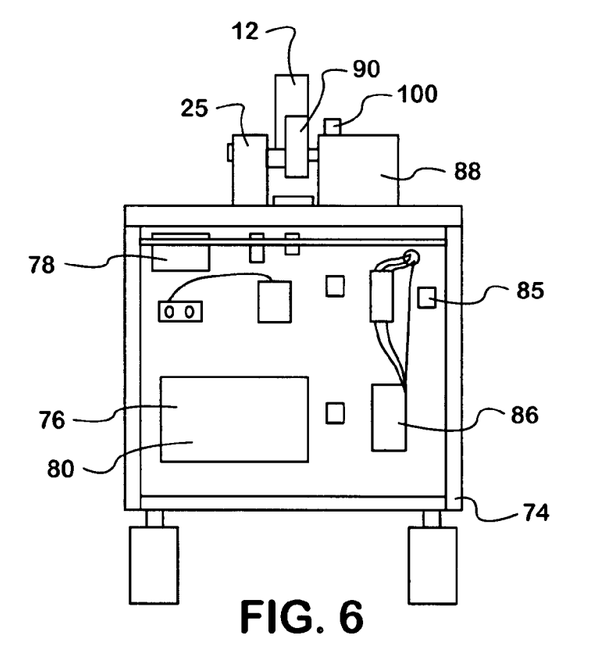
FIG. 6 is a front plan view of an abrasion resistance testing apparatus of the invention with the cabinet door and most of the wiring removed.
Figure 7:
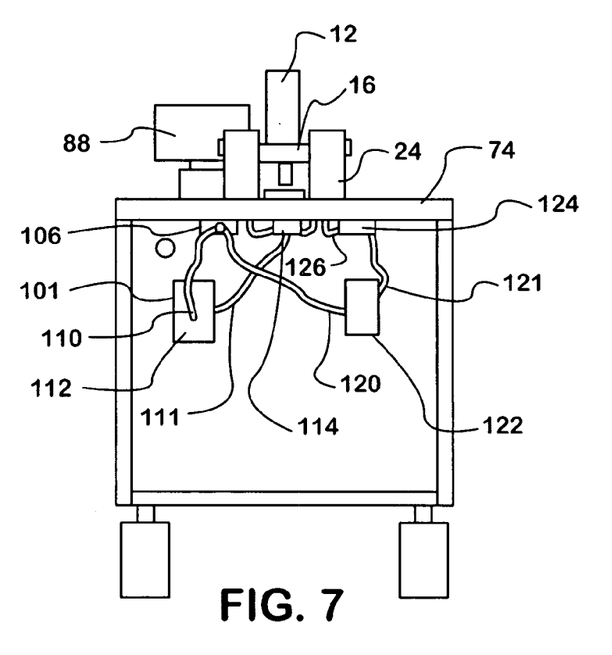
FIG. 7 is a rear plan view of an abrasion resistance testing apparatus of the invention with the moving mechanism, wiring and most of the pneumatic lines removed.

A cylindrical test sample 48, such as a length of hose, is tested to failure with the abrasion resistance testing apparatus 10. In this disclosure, the terms "tubing" and "hose" are used interchangeably. The test sample 48 can be weighed before fitting onto a hollow lightweight mandrel 50 to form a test piece 52. The mandrel 50 is fenestrated and preferably aluminum with a length of about 150 mm and an outer diameter sized to allow the cylindrical test sample 48 to fit snugly on the mandrel 50. Preferably fittings 54, 55, such as quick connect fittings, attach to the test piece 52 at each end 56, 57. A first fitting 54 connects the test piece 52 to an input pneumatic line 126.

A test piece sensor 58 attaches to the distal end 57 of the test piece 52 with a second fitting 55. Alternatively, the test piece sensor 58 can attach to an output pneumatic line leading from the distal end 57 of the test piece 52 (not shown). The test piece sensor 58 communicates with the electronic controller 76 and is preferably a pressure transducer in fluid communication with the test piece 58 for measuring a change in pressure. More preferably the test piece sensor has adjustable settings which can be preset to fail when pressure reaches the set point and communicate the failure to the electronic controller 76. The adjustable settings can be manual or electronic, depending on the test piece sensor 58.

The test piece 52 rests on a support 60. While the support 60 can be flat, the support 60 is preferably angled like a cradle when testing cylindrical items. Braces 62 at each end 56,57 of the test piece 52 immobilize the test piece 52 on the support 60 during testing.

The support 60 rests on a moveable lift plate 66 which is preferably part of the base 64. The lift plate 66 moves vertically independent of the base 64. Because the lift plate 66 moves the support up and down, test pieces having different outer diameters can be tested without changing the support 60. The outer diameter of the test pieces ranges from about 0.25 in. to about 8 in. The moving mechanism 68 for the lift plate 66 should have no backlash and is preferably a screw lift 69 with a wheel 70 and screw 72. The screw lift 69 cannot turn on its own and thus cannot move during testing.

The base 64 preferably supports the electronic controller 76 and the pneumatic system 101. The base 64 is preferably a cart 74 containing the abrading tool 12, the electronic controller 76, the motor 88 and the pneumatic system 101. A cabinet 75 located on the cart 74 encloses most of the electronic controller 76. The cart should have wheels and brakes, preferably pneumatic wheels.

The motor 88, such as a three-phase motor, has a drive cam 90 attached to a crank 92. A motor controller 86, such as an alternating current (A/C) drive, connects to the motor 88 and controls the motor speed. The distal end 94 of the crank 92 attaches to a linker 96. The linker 96 links to the platform 14 of the abrading device 12. The linker 96 can include a clevis 98 connecting to a platform projection 15 with a cotter pin 99. The linkage between the crank 92 and the abrading device 12 adjusts to vary the length of the cycle the abrading device 12 moves by varying the size of the linker 96. The cycle length varies from a maximum length of about 7 in. to a minimum length of about 2.5 in. The cycle is sinusoidal with a frequency of about 1.25 Hz which can be increased or decreased by changing the motor controller 86.

A cycle counter 100, such as a proximity sensor, measures the cycles from the drive cam 90 and can communicate with the electronic controller 76. Alternatively, the cycle counter can attach to an arm connected to the drive cam 90 to track the drive cam's revolutions. The cycle counter can be preset to terminate the test after completing the specified number of cycles. Alternatively, a timer could be used to terminate the test after a set period of time has passed.

Figure 9:
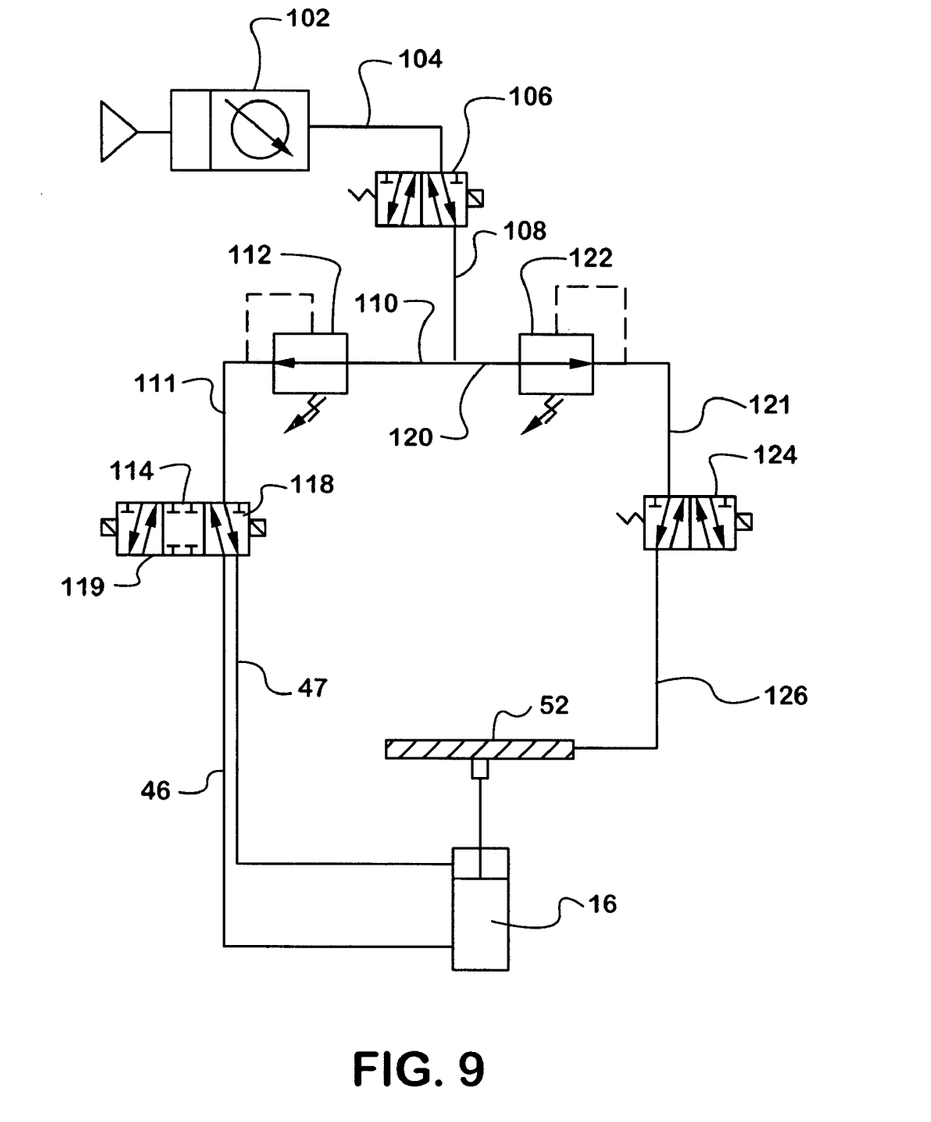
FIG. 9 is a diagram of the pneumatic control system with pneumatic lines using standard pneumatic industry symbols for an abrasion resistance testing apparatus of the invention.

Preferably, the abrading device 12 is pneumatically controlled with the pneumatic system 101. A pneumatic fluid such as pressurized air enters the apparatus 10 through a regulator 102, such as a pressure regulator valve, to adjust the pressure of the incoming pneumatic fluid. The regulator 102 can attach to the base 64. An incoming pneumatic line 104 from the regulator 102 extends to a pneumatic first valve 106. The first valve 106 is preferably a three-way, two position solenoid activated pneumatic valve.

Pneumatic fluid leaves the first valve 106 and is split between two lines, a first cylinder line 110 and a first mandrel line 120. A T-connector can be used to split the pneumatic fluid.

The first mandrel line 120 connects to a pneumatic first mandrel valve 122, such as a proportional valve. A second mandrel line 121 extends from the first mandrel valve 122 to a pneumatic second mandrel valve 124. The second mandrel valve 124 is preferably a three-way, two position solenoid-activated valve in communication with the electronic controller. An input pneumatic line 126 extends from the second mandrel valve 124 to the mandrel 50.

The first cylinder line 110 connects to a first cylinder valve 112, such as a pneumatic cylinder proportional valve. A second cylinder line 111 leaves the first cylinder valve 112 and connects to a pneumatic second cylinder valve 114. The second cylinder valve 114 is preferably a five-way, three position solenoid-activated valve. An input cylinder line 46 extends from the second cylinder valve 114 to the cylinder inlet 116 of the pneumatic cylinder 16. An output cylinder line 47 extends from the cylinder outlet 117 to the second cylinder valve 114.

Figure 8:
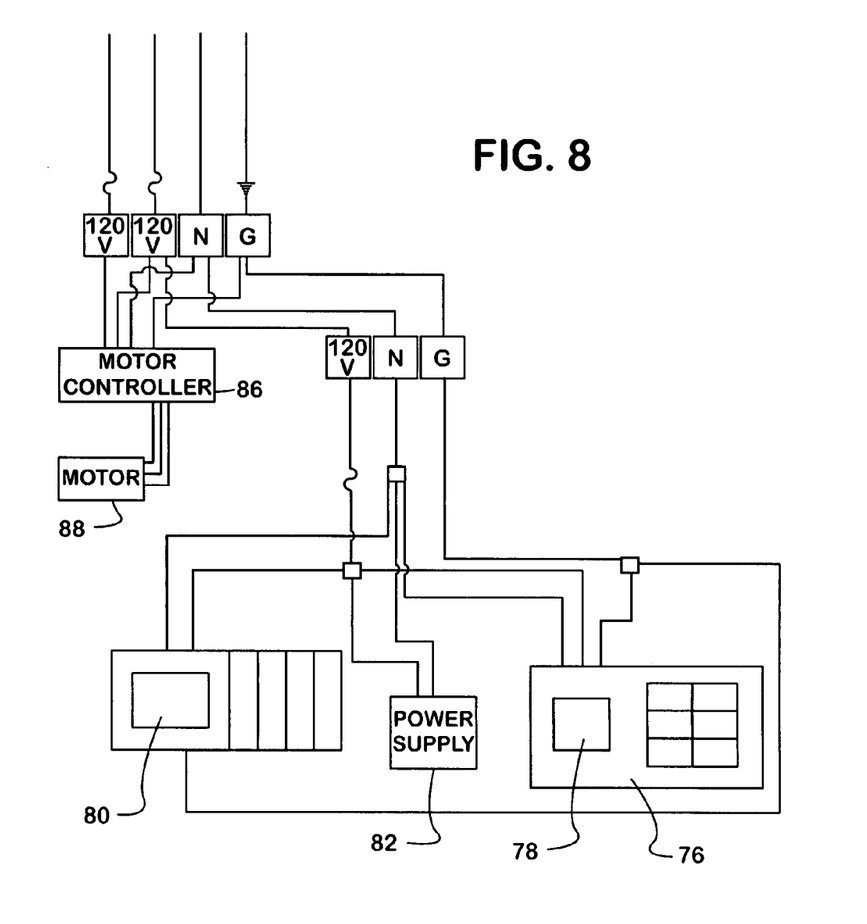
FIG. 8 is a wiring diagram using standard industry symbols for one configuration of an abrasion resistance testing apparatus of the invention.

The electronic controller 76 controls the testing of the abrasion resistance testing apparatus. The electronic controller 76 communicates with the sensors, the valves of the pneumatic system and can communicate with the motor controller 86 drive for the motor 88. The electronic controller 76 has circuitry which can be changed or reprogrammed, depending on the type of sensors used and the manufacturer of the electronic controller 76. One example of an electronic controller is a programmable logic controller (PLC), such as an Allen-Bradley 5/03 processor. The electronic controller 76 has a user interface 78, such as a touch screen, keyboard or mouse accessible to the user from outside of the cabinet 75. The interface 78 connects to a programmable system 80, such as I/O cards, memory chip, computer, and the like, and a power supply 82 located within the cabinet 75. Once set by the user, the programmable system 80 can control the sensors, valves and the cycle of the motor. The programmable system 80 can also record the output from the sensors, such as pressure, and the cycles the abrading device 12 travels. If desired, the programmable system 80 can communicate with another computer, such as a computer network.

The power supply 82 has a power cord for connecting to a power source, such as an electrical outlet or battery. A switch 85 can turn on and off the power to the power supply 82 once connected to a power source. A disconnect can attach to the cabinet door 73 to engage the switch 85 to cut-off the power when the cabinet door 73 is open. The motor controller 86 can also communicate with the electronic controller.

Power is supplied to the abrasion resistance testing apparatus 10 during testing. When the switch 85 is activated, power is available for the electronic controller 76, the interface 78, and other electrical parts of the apparatus, such as the motor controller 86 and the motor 88. Auxiliary controls, such as control buttons located on the outside of the cabinet 75, can be used to start the testing.

Before starting the test, the user presets a number of parameters. The user presets the static vertical force for the test, typically using the interface 78 of the electronic controller 76. This force will be measured by the sensor cell 32. The test piece sensor 58 is preset to a desired pressure for the test, typically with the test piece sensor 58 itself, although the electronic controller could be used to preset the desired pressure. This preset pressure determines an end point for shut off when the test sample fails. The user also presets an alternate end point for shut off as a maximum number of cycles completed by the abrading tool 18 or a set period of time.

Once the abrasion resistance testing apparatus 10 is switched on, pneumatic fluid, such as pressurized air, comes in through the regulator 102 and flows through the incoming line 104 to the first valve 106. After leaving the first valve 106, the air splits off to flow into the first mandrel valve 122 for the test piece 52 and the first cylinder valve 112 for the pneumatic cylinder 16. The electronic controller 76 can communicate with the first mandrel valve 122 to regulate the air pressure leaving the first mandrel valve 122. Air leaving the first mandrel valve 122 flows into the second mandrel valve 124, which is activated to open by the electronic controller 76. Once the second mandrel valve 124 is activated by the electronic controller 76, the air flows into the mandrel 50 at the specified pressure and pressurizes the test piece 52. The test sample 48 blocks the outflow of air from the windows 51 of the mandrel 50. Generally, the specified pressure is low (for example, 6 psi), but the specified pressure depends on the type of specimen tested.

The test piece sensor 58 attaches to the test piece 52 opposite the input air line 126 on the test piece 52. The test piece sensor 58 is set to a desired set point (for example, 4 psi). The test piece sensor 58 communicates an output signal to the electronic controller 76, typically in psi. Once the test piece 52 is fully pressurized, the electronic control 76 deactivates or closes the second mandrel valve 124 and can send further feedback to the first mandrel valve 124.

After the test piece 52 pressurizes, air leaves the first cylinder valve 112 and flows into the second cylinder valve 114. The electronic controller 76 can communicate with the first cylinder valve 112 to regulate the air pressure leaving the first cylinder valve 122. The second cylinder valve 114 is now activated or opened by the electronic controller 76 and opens the cylinder inflow 118 to allow air to flow into the pneumatic cylinder 16. The cylinder outflow 117 is closed. The air flow into the pneumatic cylinder 16 extends the piston 42, which in turn pushes the plate 40 and the abrading tool 18 down onto the test piece 52 at a specified force. The sensor cell 32 measures the force the pneumatic cylinder 16 exerts on the abrading tool 18. The electronic controller 76 can calculate the force applied and can adjust the force to the set force by adjusting the air flowing into the pneumatic cylinder 16

The testing starts with the abrading device 12 lowered onto the center of the test piece 52. The motor 88 turns on, such as with a signal from the electronic controller 76. The abrading device 12 moves back and forth in a linear motion against the test piece 52. The drive cam 90 pulls the crank 92 in a first direction to the first maximum a in the first half of a stroke, which slides the abrading 12 device along the rails 20. Then, the drive cam 90 pushes the crank 92 in a second direction through the center of the test piece 52 to the second maximum α' during the second half of the stroke and back to center. The cycle counter 100 counts one cycle. The maxima a and α' are calculated from the center of the test piece 52. Adjusting the linkage of the crank 92 with the abrading device 12, adjusts the maxima α' and α'.

When the abrading tool 18 degrades the test sample 48, the test sample 48 fails. Air flows out the windows 51 of the mandrel 50, causing the air pressure to drop. The test piece sensor 58 measures this pressure drop. Once the pressure drops to the set end point, typically about 2 psi below the set point, the test piece sensor 58 signals the electronic controller 76 to shut off the apparatus 10. Alternatively, if the test sample 48 does not fail, the electronic controller 76 can shut down the apparatus 10 once reaching the alternative end point of a preset number of cycles counted by the cycle counter 100 or a set period of time.

During shut down, the electronic controller 76 communicates with the second cylinder valve 114 to open the cylinder outflow 119. Air now flows from the pneumatic cylinder 16 to depressurize the pneumatic cylinder 16. The piston 42, plate 40 and abrading tool 18 retract and remove the force from the test piece 52. The test piece 52 can now be removed and reweighed to determine the amount of degradation of the test sample.

During use, power is supplied to the abrasion resistance testing apparatus 10. When the switch 85 is activated, power is supplied to the electronic controller 76, the interface 78, the motor controller 86 and the motor 88. The user can use the interface 78 to set and control the testing conditions, as well as starting and stopping of the motor 88, pressurizing the test piece 52, activating the pneumatic cylinder 16, and the like. Auxiliary controls, such as control buttons located on the outside of the cabinet 75, can be used to start the testing.

The proportional valves are preferably electro-pneumatic pressure regulators. The proportional valves contain electrical components communicating with the electronic controller and a pressure regulator controlling the air pressure. The proportional valves contain an air valve with an intake and one or more outtakes. The proportional valves can attach to the rear wall of the cabinet.

The first valve 106, the cylinder second valve 114 and the mandrel second valve are preferably solenoid valves which open or close when the electronic controller 76 cuts off the power to the valve. These valves can attach directly to the underside of the top of the cart or to a cross beam attached to the underside of the top of the cart. The pneumatic valves should have a long cycle life, require no lubrication and have bi-directional spool seals.

The abrasion resistance testing apparatus can be used to test a variety of test samples, typically upholstery fabrics, synthetic or natural rubbers, corrugated or braided tubing, other organic based materials, and the like. Replacing the cradle shaped support with a flat support and adjusting the height of the platform can allow the testing of a flat test sample. A flat test sample would require either a different type of sensor, such as an electrical sensor sensing current flow, to shut off the apparatus when the material fails. Alternatively, the user can manually monitor the test sample for failure and manually shut off the system.

Alternatively, a fabric test sample can be sewn into a cylindrical shape to fit a mandrel. A plastic or rubber test sample can be made into a cylindrical shape for testing. The test sample can then be fitted onto the mandrel. When using a fenestrated mandrel, a porous test sample may first fit over a thin layer of material that will easily fail under the force of the abrasion tool, such as plastic or rubber. These cylindrical test samples are then tested on the cradle shaped support.

For some materials, it may be necessary to change the type of abrading tip. This change is easily done by swapping one abrading tool from the plate with another abrading tool. Alternatively, the abrading tip of the abrading tool can be removed from the sensor cell and swapped with another abrading tip.

The abrasion resistance testing apparatus of the invention has a number of advantages. One of the advantages of the abrasion resistance testing apparatus of the invention is the automatic shut off when the test sample fails. This allows a user to run the testing without babysitting the apparatus.

Another advantage of the abrasion resistance testing apparatus is the apparatus measures the actual force applied to the test sample by the abrading tip. The user does not have to guess at the amount of force applied to the test piece. In addition, if the force is too great or insufficient, the user can adjust the applied force using the electronic controller to adjust the pressure in the pneumatic cylinder lines. The abrasion resistance apparatus automatically shuts off when the test sample fails when using the pressurized system.

Still, another advantage of the invention is the abrasion resistance testing apparatus is used with test samples with a variety of outer diameters, materials and shapes. This eliminates the need for purchasing or building many different machines to test the abrasion resistance of different samples.

The abrasion resistance testing apparatus of the invention is portable. The cart easily rolls from one location to another. This allows the user to test samples without taking up valuable counter space. In addition, when there is no need to test samples, the cart is rolled out of the way and can be stored without requiring the apparatus to be broken down.

While the invention is shown in only one of its forms, it is not thus limited but is susceptible to various changes and modifications without departing from the spirit and scope of the invention.

What is claimed is:

1. An abrasion resistance testing apparatus, comprising:
   an electronic controller;
   an abrading tool having a sensor cell communicating with the electronic controller;
   a pneumatic cylinder having a plate fastening to the abrading tool, and a piston connecting to the plate;
   a pneumatic system in fluid communication with the pneumatic cylinder and communicating with the electronic controller;
   a platform supporting the pneumatic cylinder;
   rails slidingly engaging opposite sides of the platform;
   a base;
   rail support attaching to opposite ends of the rails and connecting to the base; and
   a motor attaching to the platform.

2. The abrasion resistance testing apparatus of claim 1, wherein the motor further comprises:
   a drive cam;
   a crank extending from the drive cam; and
   a linker attaching the crank to the platform.

3. The abrasion resistance testing apparatus of claim 2, wherein the electronic controller further comprises:
   an interface; and
   a programmable system communicating with the interface and the sensor cell.

4. The abrasion resistance testing apparatus of claim 3, wherein the pneumatic system further comprises:
   valves communicating with the electronic controller.

5. The abrasion resistance testing apparatus of claim 4, wherein the platform further comprises:
   sliders attaching to the opposite sides of the platform and slidingly engaging the rails.

6. The abrasion resistance testing apparatus of claim 5 further comprising:
   a fenestrated mandrel in fluid communication with the pneumatic system; and
   a test piece sensor in fluid communication with the mandrel and communicating with The electronic controller.

7. The abrasion resistance testing apparatus of claim 6, further comprising:
   a moveable lift plate in the base supporting the mandrel.

8. The abrasion resistance testing apparatus of claim 7, wherein the abrading tool further comprises:
   an abrading tip having a rectangular top, and an slanted bottom having a curved tip, the slanted bottom slanting from the top to the curved tip; and
   a tip connector connecting The sensor cell to the abrading tip.

9. The abrasion resistance testing apparatus of claim 8, wherein the sensor cell is a pancake load cell.

10. The abrasion resistance testing apparatus of claim 8, wherein the test piece sensor is a pressure transducer.

* * * * *